(12) United States Patent
Pagès et al.

(10) Patent No.: US 8,834,402 B2
(45) Date of Patent: Sep. 16, 2014

(54) SYSTEM AND METHOD FOR THE RE-ANTICOAGULATION OF PLATELET RICH PLASMA

(75) Inventors: Etienne Pagès, Cessy (FR); Michael Ragusa, Hingham, MA (US)

(73) Assignee: Haemonetics Corporation, Braintree, MA (US)

( * ) Notice: Subject to any disclaimer, the term of this patent is extended or adjusted under 35 U.S.C. 154(b) by 491 days.

(21) Appl. No.: 12/402,565

(22) Filed: Mar. 12, 2009

(65) Prior Publication Data
US 2010/0234788 A1 Sep. 16, 2010

(51) Int. Cl.
| | |
|---|---|
| A61M 37/00 | (2006.01) |
| A61M 1/36 | (2006.01) |
| A61M 1/28 | (2006.01) |
| A61M 1/02 | (2006.01) |
| A61M 5/14 | (2006.01) |

(52) U.S. Cl.
CPC .............. *A61M 1/3643* (2013.01); *A61M 1/288* (2013.01); *A61M 1/0209* (2013.01); *A61M 1/3693* (2013.01); *A61M 1/3672* (2013.01); *A61M 2005/1402* (2013.01); *A61M 2005/1403* (2013.01); *A61M 2202/0427* (2013.01)
USPC .......... 604/6.04; 604/4.01; 604/6.07; 604/6.1; 604/6.11; 604/6.15; 422/44

(58) Field of Classification Search
CPC .............. A61M 2005/1402; A61M 2005/1403; A61M 1/3627; A61M 1/3643; A61M 1/288; A61M 1/3629; A61M 1/3644; A61M 1/3646; A61M 1/3649; A61M 1/365; A61M 1/0209; A61M 1/3693; A61M 1/3672; A61M 2202/0427

USPC ........... 604/4.01, 6.01, 6.02, 6.03, 6.04, 6.07, 604/6.11; 422/44
See application file for complete search history.

(56) References Cited

U.S. PATENT DOCUMENTS

| | | |
|---|---|---|
| 1,025,059 A | 4/1912 | Hatton et al. |
| 1,611,725 A | 12/1926 | Degerth et al. |

(Continued)

FOREIGN PATENT DOCUMENTS

| | | | |
|---|---|---|---|
| EP | 0 128 683 | 12/1984 | .............. A61M 1/03 |
| EP | 0 171 749 | 2/1986 | .............. A61M 1/00 |

(Continued)

OTHER PUBLICATIONS

"Prime—definition of prime by the Free Online Dictionary, Thesaurus and Encyclopedia." http://www.thefreedictionary.com/prime. Accessed Sep. 17, 2013.*

(Continued)

*Primary Examiner* — Adam Marcetich
(74) *Attorney, Agent, or Firm* — Sunstein Kann Murphy & Timbers LLP

(57) ABSTRACT

A method for the re-anticoagulation of platelet rich plasma in a blood apheresis system includes priming the blood apheresis system with anticoagulant, such that a volume of anticoagulant is transferred to a PRP container. The method may then transfer the anticoagulant within the PRP container to a red blood cell container, and collect a volume of platelet rich plasma within the PRP container. The platelet rich plasma may be collected in a plurality of cycles. Between collection cycles, the method may transfer a portion of the volume of anticoagulant from the red blood cell container to the PRP container.

10 Claims, 4 Drawing Sheets

(56) References Cited

U.S. PATENT DOCUMENTS

| | | | | |
|---|---|---|---|---|
| 2,087,778 | A | 7/1937 | Nelin et al. | 210/64 |
| 2,661,150 | A | 12/1953 | Abbott, Jr. | 233/27 |
| 2,750,107 | A | 6/1956 | More | 233/2 |
| 2,792,172 | A | 5/1957 | Tait | 233/2 |
| 3,096,283 | A | 7/1963 | Hein | 233/20 |
| 3,145,713 | A | 8/1964 | Latham | 128/214 |
| 3,239,136 | A | 3/1966 | Hein | 233/20 |
| 3,244,362 | A | 4/1966 | Hein | 233/27 |
| 3,244,363 | A | 4/1966 | Hein | 233/28 |
| 3,409,213 | A | 11/1968 | Latham, Jr. | 233/21 |
| 3,456,875 | A | 7/1969 | Hein | 233/24 |
| 3,489,145 | A | 1/1970 | Judson et al. | 128/214 |
| 3,565,330 | A | 2/1971 | Latham, Jr. | 233/21 |
| 3,655,058 | A | 4/1972 | Novak | 210/360 |
| 3,737,096 | A | 6/1973 | Jones et al. | 233/19 A |
| 3,774,840 | A | 11/1973 | Boatright | 233/14 R |
| 3,987,961 | A | 10/1976 | Sinn et al. | 233/27 |
| 4,007,871 | A | 2/1977 | Jones et al. | 233/27 |
| 4,010,894 | A | 3/1977 | Kellogg et al. | 233/27 |
| 4,014,497 | A | 3/1977 | Spiewok et al. | 233/20 R |
| 4,040,965 | A | 8/1977 | Kohlheb | 210/297 |
| 4,056,224 | A | 11/1977 | Lolachi | 233/14 R |
| 4,082,217 | A | 4/1978 | Westberg | 233/25 |
| 4,086,924 | A | 5/1978 | Latham, Jr. | 128/214 R |
| 4,140,268 | A | 2/1979 | Lacour | 233/1 |
| 4,142,670 | A | 3/1979 | Ishimaru et al. | 233/20 R |
| 4,151,844 | A | 5/1979 | Cullis et al. | 128/214 R |
| 4,197,847 | A | 4/1980 | Djerassi | 128/214 R |
| 4,285,464 | A | 8/1981 | Latham, Jr. | 233/26 |
| 4,300,717 | A | 11/1981 | Latham, Jr. | 233/1 A |
| 4,303,193 | A | 12/1981 | Latham, Jr. | 233/23 A |
| 4,321,921 | A | 3/1982 | Laszczower | 128/276 |
| 4,387,848 | A | 6/1983 | Kellogg et al. | 494/81 |
| 4,416,654 | A | 11/1983 | Schoendorfer et al. | 494/10 |
| 4,425,114 | A | 1/1984 | Schoendorfer et al. | 604/7 |
| 4,430,072 | A | 2/1984 | Kellogg et al. | 494/45 |
| 4,447,221 | A | 5/1984 | Mulzet | 494/45 |
| 4,457,747 | A | 7/1984 | Tu | 604/4 |
| 4,464,167 | A | 8/1984 | Schoendorfer et al. | 604/6 |
| 4,466,888 | A | 8/1984 | Verkaart | 210/232 |
| 4,482,342 | A | 11/1984 | Lueptow et al. | 494/21 |
| 4,530,691 | A | 7/1985 | Brown | 494/45 |
| 4,534,863 | A | 8/1985 | Bacon et al. | 210/232 |
| 4,643,714 | A | 2/1987 | Brose | 604/4 |
| 4,647,279 | A | 3/1987 | Mulzet et al. | 494/45 |
| 4,670,013 | A | * | 6/1987 | Barnes et al. | 604/403 |
| 4,680,025 | A | 7/1987 | Kruger et al. | 604/6 |
| 4,684,361 | A | 8/1987 | Feldman et al. | 494/41 |
| 4,692,136 | A | 9/1987 | Feldman et al. | 494/38 |
| 4,708,712 | A | 11/1987 | Mulzet | 494/45 |
| 4,713,176 | A | 12/1987 | Schoendorfer et al. | 210/645 |
| 4,734,089 | A | 3/1988 | Cullis | 494/27 |
| 4,740,202 | A | 4/1988 | Stacey et al. | 604/119 |
| 4,740,313 | A | 4/1988 | Schoendorfer et al. | 210/651 |
| 4,755,300 | A | 7/1988 | Fischel et al. | 210/650 |
| 4,767,396 | A | 8/1988 | Powers | 494/60 |
| 4,795,419 | A | 1/1989 | Yawn et al. | 494/84 |
| 4,795,448 | A | 1/1989 | Stacey et al. | 604/319 |
| 4,806,247 | A | 2/1989 | Schoendorfer et al. | 210/321.18 |
| 4,806,252 | A | 2/1989 | Brown et al. | 210/744 |
| 4,808,307 | A | 2/1989 | Fischel et al. | 210/321.68 |
| 4,850,995 | A | 7/1989 | Tie et al. | 604/6 |
| 4,869,812 | A | 9/1989 | Schoendorfer et al. | 210/321.63 |
| 4,871,462 | A | 10/1989 | Fischel et al. | 210/651 |
| 4,876,013 | A | 10/1989 | Shmidt et al. | 210/650 |
| 4,889,524 | A | 12/1989 | Fell et al. | 494/12 |
| 4,911,833 | A | 3/1990 | Schoendorfer et al. | 210/167 |
| 4,934,995 | A | 6/1990 | Cullis | 494/45 |
| 4,940,543 | A | 7/1990 | Brown et al. | 210/369 |
| 4,943,273 | A | 7/1990 | Pages | 494/41 |
| 4,968,295 | A | 11/1990 | Neumann | 604/6 |
| 4,983,156 | A | 1/1991 | Knelson | 494/28 |
| 4,983,158 | A | 1/1991 | Headley | 494/41 |
| 4,985,153 | A | * | 1/1991 | Kuroda et al. | 210/782 |
| 4,994,188 | A | 2/1991 | Prince | 210/636 |
| 5,039,401 | A | 8/1991 | Columbus et al. | 210/117 |
| 5,045,048 | A | 9/1991 | Kaleskas et al. | 494/41 |
| 5,098,372 | A | 3/1992 | Jonsson | 604/5 |
| 5,100,372 | A | 3/1992 | Headley | 494/41 |
| 5,100,564 | A | 3/1992 | Pall et al. | 210/782 |
| 5,112,298 | A | 5/1992 | Prince et al. | 604/6 |
| 5,114,396 | A | 5/1992 | Unger et al. | 494/37 |
| 5,135,667 | A | * | 8/1992 | Schoendorfer | 210/782 |
| 5,141,486 | A | 8/1992 | Antwiler | 494/37 |
| 5,147,290 | A | 9/1992 | Jonsson | 604/5 |
| 5,154,716 | A | 10/1992 | Bauman et al. | 604/410 |
| 5,171,456 | A | * | 12/1992 | Hwang et al. | 210/782 |
| 5,174,894 | A | 12/1992 | Ohsawa et al. | 210/86 |
| 5,194,145 | A | 3/1993 | Schoendorfer | 210/90 |
| 5,217,426 | A | 6/1993 | Bacehowski et al. | 494/45 |
| 5,217,427 | A | 6/1993 | Cullis | 494/45 |
| 5,234,403 | A | 8/1993 | Yoda et al. | 604/4 |
| 5,254,248 | A | 10/1993 | Nakamura | 210/321.67 |
| 5,269,946 | A | * | 12/1993 | Goldhaber et al. | 210/767 |
| 5,273,517 | A | 12/1993 | Barone et al. | 494/37 |
| 5,277,701 | A | 1/1994 | Christie et al. | 604/4 |
| 5,298,016 | A | 3/1994 | Gordon | 604/4 |
| 5,298,171 | A | 3/1994 | Biesel | 210/739 |
| 5,300,060 | A | 4/1994 | Nelson | 604/410 |
| 5,311,908 | A | 5/1994 | Barone et al. | 137/881 |
| 5,316,540 | A | 5/1994 | McMannis et al. | 494/37 |
| 5,318,512 | A | 6/1994 | Neumann | 604/6 |
| 5,348,533 | A | 9/1994 | Papillon et al. | 604/4 |
| 5,368,542 | A | 11/1994 | McMannis et al. | 494/45 |
| 5,370,802 | A | 12/1994 | Brown | 210/782 |
| 5,386,734 | A | 2/1995 | Pusinelli | 73/863.21 |
| 5,387,174 | A | 2/1995 | Rochat | 494/10 |
| 5,387,187 | A | 2/1995 | Fell et al. | 604/6 |
| 5,403,272 | A | 4/1995 | Deniega et al. | 604/4 |
| 5,405,308 | A | 4/1995 | Headley et al. | 494/67 |
| 5,417,650 | A | 5/1995 | Gordon | 604/4 |
| 5,427,695 | A | * | 6/1995 | Brown | 210/805 |
| 5,431,814 | A | 7/1995 | Jorgensen | 210/399 |
| 5,437,598 | A | 8/1995 | Antwiler | 494/1 |
| 5,437,624 | A | 8/1995 | Langley | 604/4 |
| 5,462,667 | A | 10/1995 | Wollinsky et al. | 210/645 |
| 5,470,483 | A | 11/1995 | Bene et al. | 210/741 |
| 5,484,396 | A | 1/1996 | Naficy | 604/4 |
| 5,494,592 | A | 2/1996 | Latham, Jr. et al. | 210/805 |
| 5,505,685 | A | 4/1996 | Antwiler | 494/37 |
| 5,514,070 | A | 5/1996 | Pages | 494/41 |
| 5,543,062 | A | 8/1996 | Nishimura | 210/782 |
| 5,551,941 | A | 9/1996 | Howell | 494/16 |
| 5,585,007 | A | 12/1996 | Antanavich et al. | 210/782 |
| 5,607,579 | A | 3/1997 | Latham, Jr. et al. | 210/195.1 |
| 5,614,106 | A | * | 3/1997 | Payrat et al. | 210/767 |
| 5,616,254 | A | * | 4/1997 | Pall et al. | 210/806 |
| 5,649,903 | A | 7/1997 | Deniega et al. | 604/4 |
| 5,651,766 | A | 7/1997 | Kingsley et al. | 604/6 |
| 5,656,163 | A | 8/1997 | Brown | 210/360.1 |
| 5,728,060 | A | 3/1998 | Kingsley et al. | 604/4 |
| 5,733,253 | A | 3/1998 | Headley et al. | 604/4 |
| 5,733,446 | A | 3/1998 | Holm | 210/206 |
| 5,733,545 | A | 3/1998 | Hood, III | 424/93.72 |
| 5,738,792 | A | 4/1998 | Schoendorfer | 210/651 |
| 5,753,428 | A | 5/1998 | Yuasa et al. | 435/2 |
| 5,762,791 | A | 6/1998 | Deniega et al. | 210/321.67 |
| 5,779,660 | A | 7/1998 | Kingsley et al. | 604/6 |
| 5,783,085 | A | 7/1998 | Fischel | 210/651 |
| 5,792,351 | A | 8/1998 | Wehrle et al. | 210/321.67 |
| 5,792,372 | A | * | 8/1998 | Brown et al. | 210/782 |
| 5,882,289 | A | 3/1999 | Sakota et al. | 494/37 |
| 5,899,874 | A | 5/1999 | Jonsson | 604/4 |
| 5,919,125 | A | 7/1999 | Berch | 494/67 |
| 5,964,724 | A | 10/1999 | Rivera et al. | 604/4 |
| 5,980,760 | A | 11/1999 | Min et al. | 210/782 |
| 6,007,725 | A | 12/1999 | Brown | 210/739 |
| 6,033,561 | A | * | 3/2000 | Schoendorfer | 210/195.1 |
| 6,059,979 | A | 5/2000 | Brown | 210/739 |
| 6,106,509 | A | * | 8/2000 | Loubser | 604/410 |
| 6,207,063 | B1 | 3/2001 | Brown | 210/739 |
| 6,234,989 | B1 | 5/2001 | Brierton et al. | 604/5.01 |
| 6,296,602 | B1 | 10/2001 | Headley | 494/37 |
| 6,464,624 | B2 | 10/2002 | Pages | 494/36 |

(56) References Cited

U.S. PATENT DOCUMENTS

| | | | |
|---|---|---|---|
| 6,558,307 B2 | 5/2003 | Headley | 494/37 |
| 6,582,349 B1* | 6/2003 | Cantu et al. | 494/1 |
| 6,743,192 B1* | 6/2004 | Sakota et al. | 604/6.01 |
| 6,752,777 B1* | 6/2004 | Takagi et al. | 604/6.01 |
| 6,773,413 B2* | 8/2004 | Keller et al. | 604/6.01 |
| 7,270,645 B2 | 9/2007 | Langley et al. | 604/6.01 |
| 8,454,548 B2* | 6/2013 | Ohashi et al. | 604/6.01 |
| 2001/0027156 A1 | 10/2001 | Egozy et al. | 494/37 |
| 2003/0066807 A1* | 4/2003 | Suzuki | 210/782 |
| 2003/0175150 A1* | 9/2003 | Grimm | 422/44 |
| 2003/0211927 A1* | 11/2003 | Cantu et al. | 494/3 |
| 2004/0112808 A1* | 6/2004 | Takagi et al. | 210/143 |
| 2004/0186408 A1* | 9/2004 | Behague et al. | 604/4.01 |
| 2005/0139556 A1 | 6/2005 | Bischof | 210/787 |
| 2005/0147529 A1* | 7/2005 | Westberg et al. | 422/44 |
| 2005/0209522 A1* | 9/2005 | Tadokoro et al. | 600/508 |
| 2005/0234385 A1* | 10/2005 | Vandlik et al. | 604/6.03 |
| 2006/0287628 A1* | 12/2006 | Hirabuki | 604/6.01 |
| 2007/0243990 A1* | 10/2007 | Kolenbrander et al. | 494/37 |
| 2008/0076114 A1 | 3/2008 | Patzke | 435/4 |
| 2008/0199845 A1 | 8/2008 | Rosiello et al. | 435/2 |
| 2008/0206858 A1* | 8/2008 | Blasetti et al. | 435/308.1 |
| 2008/0281247 A1* | 11/2008 | Tadokoro et al. | 604/5.01 |
| 2009/0259162 A1* | 10/2009 | Ohashi et al. | 604/6.01 |

FOREIGN PATENT DOCUMENTS

| | | | |
|---|---|---|---|
| EP | 0 208 061 | 1/1987 | A61M 1/34 |
| EP | 0 257 755 | 3/1988 | A61M 1/36 |
| EP | 0 308 407 | 4/1993 | A61M 1/36 |
| EP | 0 578 086 | 1/1994 | A61M 1/36 |
| EP | 0 619 145 | 10/1994 | B04B 9/12 |
| EP | 0 664 159 | 7/1995 | B04B 5/04 |
| EP | 0 754 461 | 1/1997 | A61K 35/14 |
| EP | 0 799 645 | 10/1997 | B04B 5/04 |
| EP | 0 885 619 | 12/1998 | A61M 1/36 |
| EP | 0 649 311 | 1/2000 | A61K 35/14 |
| EP | 0 992 256 | 4/2000 | A61M 1/38 |
| EP | 1 057 534 | 12/2000 | B04B 5/04 |
| EP | 1 146 895 | 11/2003 | A61K 38/19 |
| EP | 1 374 890 | 1/2004 | A61K 38/19 |
| FR | 2 258 898 | 8/1975 | B04B 1/00 |
| GB | 2 047 110 | 11/1980 | A61M 1/03 |
| JP | 59-006952 | 1/1984 | B04B 5/00 |
| JP | 59-069166 | 4/1984 | B04B 11/00 |
| JP | 07-075746 | 3/1995 | B04B 1/02 |
| JP | 08-131539 | 5/1996 | A61M 1/02 |
| JP | 09-192215 | 7/1997 | A61M 1/02 |
| SU | 660718 | 5/1979 | B04B 5/00 |
| SU | 762982 | 9/1980 | B04B 5/04 |
| SU | 1146098 | 3/1985 | B04B 5/00 |
| WO | WO 85/02561 | 6/1985 | B04B 1/10 |
| WO | WO 87/06472 | 11/1987 | A61M 1/36 |
| WO | WO 90/00059 | 1/1990 | A61K 35/14 |
| WO | WO 90/07383 | 7/1990 | B04B 7/08 |
| WO | WO 93/21935 | 11/1993 | A61K 35/14 |
| WO | WO 94/06535 | 3/1994 | B01D 33/00 |
| WO | WO 96/11747 | 4/1996 | B04B 5/04 |
| WO | WO 96/33023 | 10/1996 | B04B 5/04 |
| WO | WO 00/44398 | 8/2000 | A61K 38/19 |
| WO | WO 2006/029233 | 3/2006 | A01N 1/02 |
| WO | WO 2006/044790 | 4/2006 | C12N 5/08 |
| WO | WO 2007/047687 | 4/2007 | A61K 35/14 |

OTHER PUBLICATIONS

European Patent Office, *International Search Report and Written Opinion of the International Searching Authority*—International Application No. PCT/US2010/026186, dated Jul. 20, 2010, 2009 (10 pages).

* cited by examiner

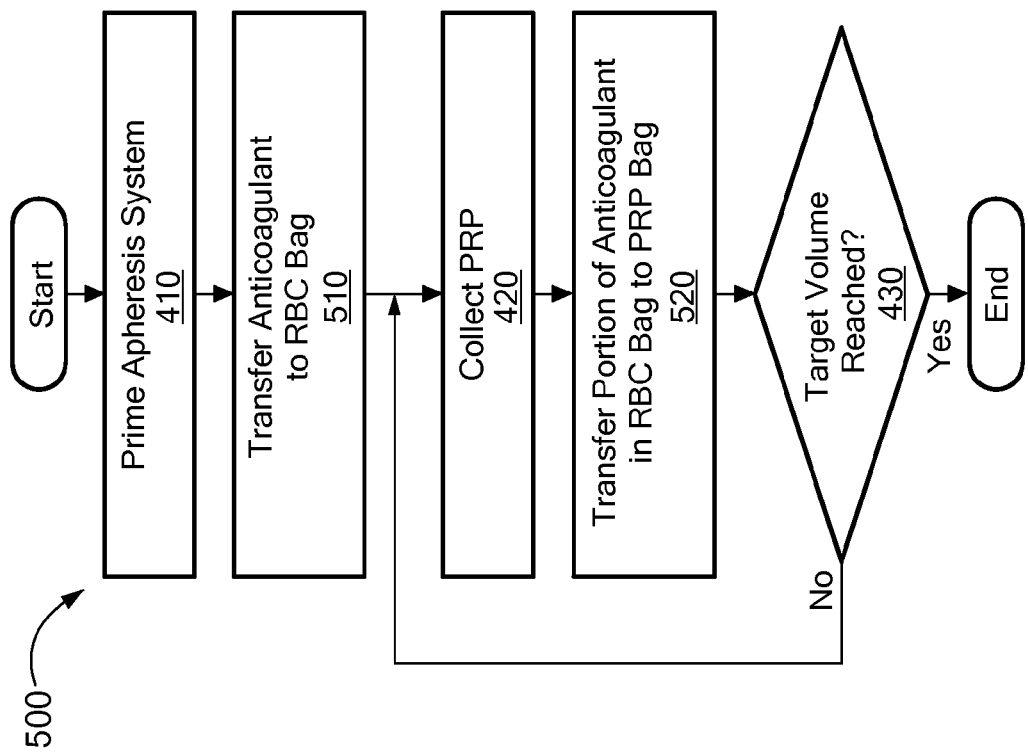
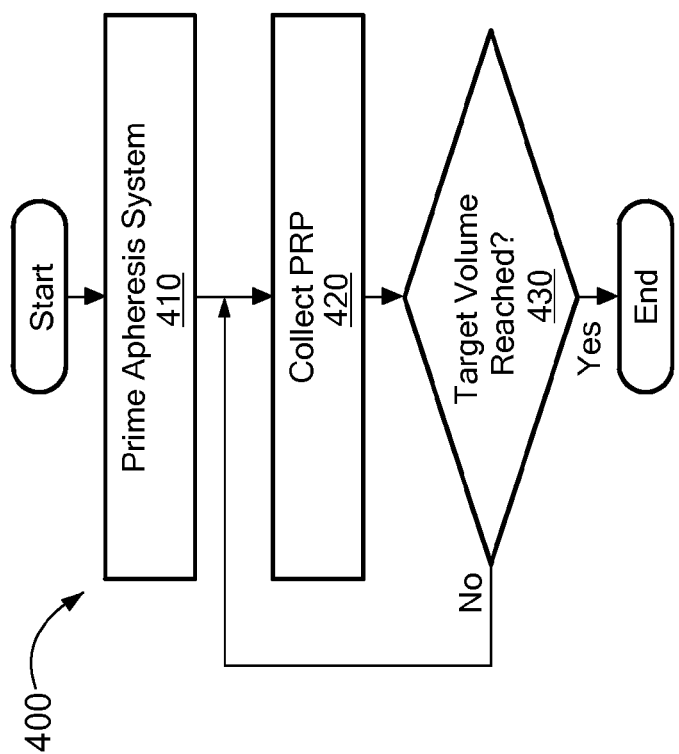

SYSTEM AND METHOD FOR THE RE-ANTICOAGULATION OF PLATELET RICH PLASMA

TECHNICAL FIELD

The present invention relates to systems and methods for platelet collection, and particularly to systems and methods for the re-anticoagulation of platelet rich plasma.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

Among various blood component products obtainable through apheresis, the demand for platelet products is rapidly growing. This is particularly because, with the improvement in cancer therapy, there is a need to administer more and more platelets to patients with lowered hemopoietic function. Platelets are fragments of a large cell located in the marrow called a megakaryocyte and primarily contribute to hemostasis by performing the aggregation function. Platelets also have a role in tissue healing. Normal platelet counts are 150,000-400,000/mm$^3$ in the adult. Platelet counts under 20,000/mm$^3$ can cause various problems such as spontaneous bleeding.

Platelets have a short half-life of 4-6 days and the number of donors is limited. Therefore, in producing plasma reduced platelet products, it is important to harvest platelets from the whole blood supplied by a donor at a maximum yield and in a required amount. Further, it is known that the contamination of plasma reduced platelet product by white blood cells can lead to serious medial complications, such as GVH reactions. Therefore, it is also very important to keep the level of contamination by white blood cells as low as possible, while efficiently collecting platelets.

To that end, various techniques have been developed. For example, using "surge" technology, after whole blood is collected and concentrically separated within a centrifuge into higher density, intermediate density and lower density components and plasma is harvested (so-called "draw" step), the plasma is supplied through the centrifuge at a surge flow rate, that is, a flow rate that increases with time. By performing the surge, platelets can be preferentially displaced from the intermediate density components, which exist as a buffy coat mainly comprising a mixture of platelets and white blood cells. Plasma reduced platelet products can thereby be produced at an increased yield.

Instead of using surge technology, the platelet layer can also be extracted from the centrifuge by means of a layer "push" in which anticoagulated whole blood is introduced into the bowl until the platelet layer is pushed out, or by using a combination of surge and push methodologies. After harvesting a desired component or components, the residual blood components mostly comprising red blood cells are returned to the donor (so-called "return" step).

Typically, 450-500 ml of whole blood is processed during one cycle which comprises the above-mentioned successive steps. This amount is based on 15% or less of the total amount of blood in humans and, if more than this amount is taken out of the body at once, the donor may suffer from blood pressure lowering or dizziness. Using surge technology, the concentration of the sequestered platelet product ranges from $0.8 \times 10^6/\mu L$ to $2.6 \times 10^6/\mu L$ (typically $1.5 \times 10^6/\mu L$), with moderate leukocyte concentration. Pushed platelet product concentration tends to be higher but leads to greater leukocyte and red blood cell residual contamination.

This resulting platelet concentration is often too low for platelet product compatibility with arising pathogen inactivation methods. Additionally, simultaneous plasma collection of one to two additional plasma units may be prevented due to the relatively high volume of plasma captured with the platelet product. The relatively high plasma protein content in the platelet product is also less desirable in terms of recipient tolerance.

Blood processing systems, such as blood apheresis systems, add a citrated anticoagulant such as ACD-A to prevent blood and blood component clumping and coagulation within the system. Typically, the anticoagulant is mixed with the whole blood drawn from the donor. The ratio of anticoagulant to whole blood must be kept below a certain threshold because most of the anticoagulant introduced into the system will be returned to the donor. If too much anticoagulant is returned to the donor, the donor may experience adverse reactions such as a citrate reaction.

SUMMARY OF THE INVENTION

In accordance with one embodiment of the present invention, a method for the re-anticoagulation of platelet rich plasma in a blood apheresis system includes collecting a volume of platelet rich plasma within a first collection container, and adding anticoagulant into the first collection container as the platelet rich plasma is being collected. The volume of platelet rich plasma may be collected in a plurality of cycles, and the anticoagulant may be added to the first collection container between each of the cycles. The method may also include priming the blood apheresis system with anticoagulant such that a volume of anticoagulant is transferred to the first collection container. The method may then transfer the anticoagulant within the first collection container to a second collection container.

In accordance with other embodiments, a method for the re-anticoagulation of platelet rich plasma in a blood apheresis system may include drawing whole blood from a donor, introducing anticoagulant into the whole blood, separating the anticoagulated whole blood into a plurality of blood components (including platelet rich plasma), and collecting the platelet rich plasma in a collection container. The method may also add anticoagulant into the collection container as the platelet rich plasma is collected. The volume of platelet rich plasma may be collected in a plurality of cycles, and the anticoagulant may be added to the collection container between each of the cycles. The method may also include priming the blood apheresis system with anticoagulant such that a volume of anticoagulant is transferred to the collection container. The method may then transfer the anticoagulant within the collection container bag to a second container.

In accordance with further embodiment of the present invention, a method for the re-anticoagulation of platelet rich plasma in a blood apheresis system includes priming the blood apheresis system with anticoagulant such that a volume of anticoagulant is transferred to a PRP collection container, and transferring the anticoagulant within the PRP collection container to a second container. The method then collects, in a number of cycles, a volume of platelet rich plasma in the PRP collection container. Between cycles of the platelet rich plasma collection process, the method transfers some of the anticoagulant from the second container to the PRP collection container. The amount of anticoagulant transferred to the PRP collection container may be proportional to the amount of platelet rich plasma collected in the preceding cycle. The total volume of anticoagulant transferred to the PRP collection container may be proportional to a target volume of platelet rich plasma, which is the sum of the volumes collected in each of the cycles.

In accordance with other embodiments, the priming process may include priming an anticoagulant line and a donor line filter with anticoagulant. The method may also transfer the anticoagulant within the donor line filter to the second container (e.g., at the start of the first platelet rich plasma collection cycle) or the method may return it to an anticoagulant source.

Each of the platelet rich plasma collections cycles may include drawing whole blood from a donor, introducing anticoagulant into the whole blood drawn from the donor, and introducing the anticoagulated whole blood into a separation chamber. The separation chamber may separate the anticoagulated whole blood into a number of blood components including platelet rich plasma. The method may then extract the platelet rich plasma from the separation chamber into the PRP collection container. The method may also reintroduce the collected platelet rich plasma into the separation chamber, which separates the reintroduced platelet rich plasma into plasma and plasma reduced platelet product. Once separated, the method may then extract the plasma reduced platelet product from the separation chamber into a platelet container. The amount of anticoagulant introduced into the whole blood upon withdrawal may be proportionately reduced by the volume of anticoagulant within the PRP collection container.

In accordance with other embodiments of the present invention, a system for the re-anticoagulation of platelet rich plasma in a blood apheresis system may include a PRP container for storing collected platelet rich plasma, and a red blood cell container for storing red blood cells. The system may also include means for priming the system with anticoagulant such that a volume of anticoagulant is transferred to the PRP container, and means for transferring the anticoagulant within the PRP container to the red blood cell container. Additionally, the system may also have means for collecting a volume of platelet rich plasma within the PRP container in a number of cycles, and means for transferring some or all of the volume of anticoagulant from the red blood cell container to the PRP container between each cycle. The volume of anticoagulant transferred to the PRP container may be proportional to the amount of platelet rich plasma collected in the preceding cycle. The total volume of anticoagulant transferred to the PRP container may be proportional to a target volume of platelet rich plasma, which is the sum of the volumes collected in each of the plurality of cycles.

The system may also prime an anticoagulant line and a donor line filter with anticoagulant. The system may transfer the anticoagulant within the donor line filter to the red blood cell container or the system may return the anticoagulant within the donor line filter to an anticoagulant source. The means for transferring the anticoagulant may transfer the anticoagulant within the donor line filter to the red blood cell container at the start of the first of the plurality of cycles.

In accordance with still further embodiments, the system may also include means for drawing whole blood from a donor, means for introducing anticoagulant into the whole blood drawn from the donor, and means for introducing the anticoagulated whole blood into a separation chamber. The separation chamber may separate the anticoagulated whole blood into a number of blood components including platelet rich plasma. The system may then extract the platelet rich plasma from the separation chamber into the PRP container. The system may also have means for reintroducing the collected platelet rich plasma into the separation chamber, which further separates the reintroduced platelet rich plasma into plasma and plasma reduced platelet product. The system may also have means for extracting the plasma reduced platelet product from the separation chamber into platelet container. The amount of anticoagulant introduced into the whole blood upon withdrawal may be proportionately reduced by the volume of anticoagulant within the PRP container.

In accordance with additional embodiments of the present invention, a method for the re-anticoagulation of platelet rich plasma in a blood apheresis system includes priming the blood apheresis system with anticoagulant such that a volume of anticoagulant is transferred to a PRP container, and collecting, in a number of cycles, a target volume of platelet rich plasma within the PRP container. The volume of anticoagulant may be proportional to the target volume of platelet rich plasma. The target volume may be the sum of the volumes collected in each of the plurality of cycles.

Priming the blood apheresis system with anticoagulant may include priming an anticoagulant line and a donor line filter with anticoagulant. The method may transfer the anticoagulant within the donor line filter to the red blood cell container (e.g., at the start of the first cycle) or return it to an anticoagulant source. Each of the cycles may include drawing whole blood from a donor, introducing anticoagulant into the whole blood, and introducing the anticoagulated whole blood into a separation chamber. The amount of anticoagulant introduced into the whole blood upon withdrawal may be proportionately reduced by the volume of anticoagulant within the PRP container.

The separation chamber may separate the anticoagulated whole blood into a number of blood components including platelet rich plasma. The method may then extract the platelet rich plasma from the separation chamber into the PRP container. After the cycles are complete and a target volume is collected, the method may reintroduce the platelet rich plasma from the PRP container into the separation chamber, which may further separate the reintroduced platelet rich plasma into plasma and plasma reduced platelet product. The method may then extract the plasma reduced platelet product from the separation chamber into a platelet container.

BRIEF DESCRIPTION OF THE DRAWINGS

The foregoing features of the invention will be more readily understood by reference to the following detailed description, taken with reference to the accompanying drawings, in which:

FIG. 4 is a flow chart depicting a method for re-anticoagulating collected platelet rich plasma, in accordance with one embodiment of the invention; and FIG. 5 is a flow chart depicting an alternative method for re-anticoagulating collected platelet rich plasma, in accordance with one embodiment of the invention.

DETAILED DESCRIPTION OF SPECIFIC EMBODIMENTS

Figure 1:
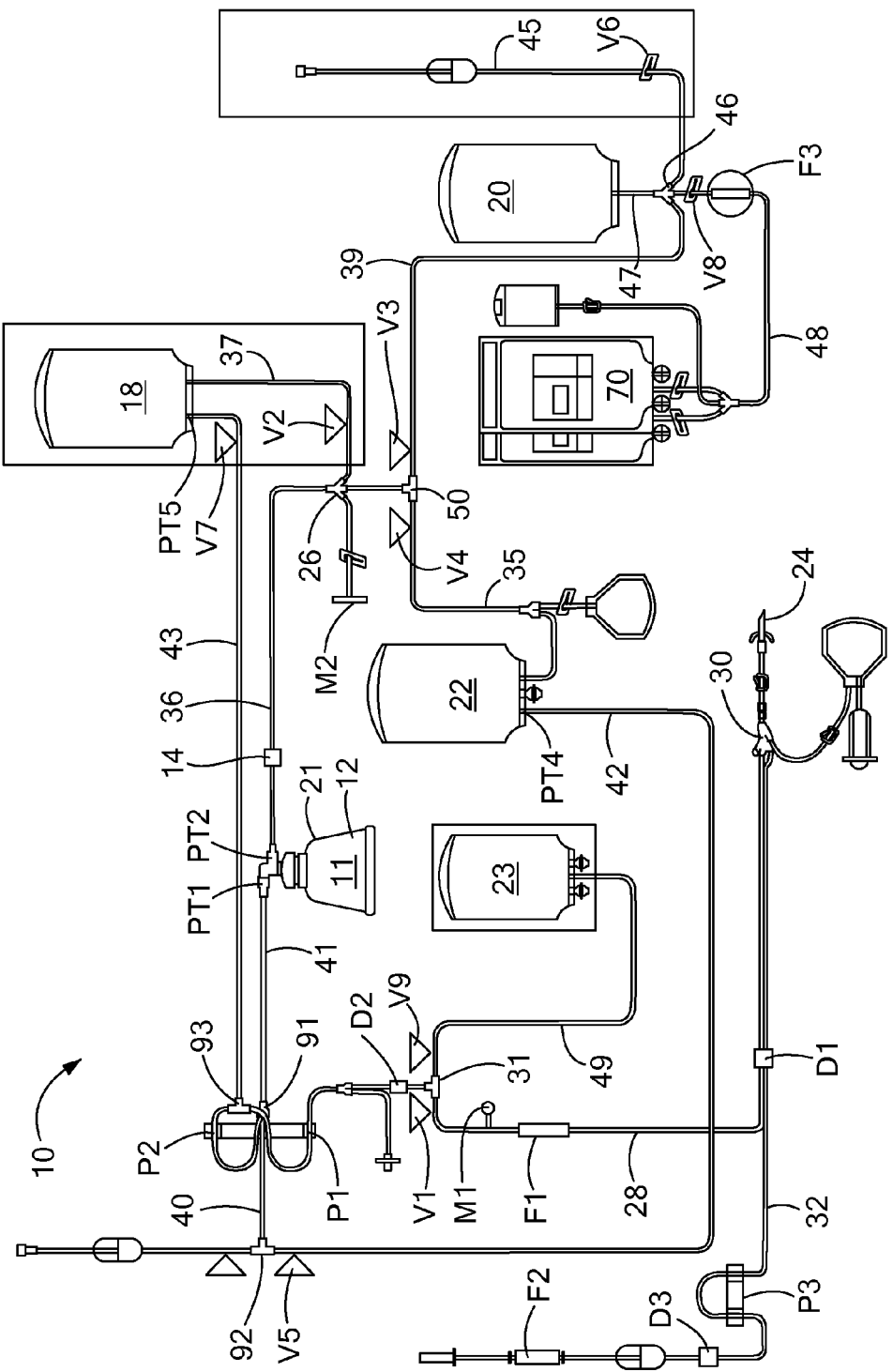
FIG. 1 is a schematic diagram of a system for use with an apheresis machine, in accordance with one embodiment of the invention.
Figure 2:
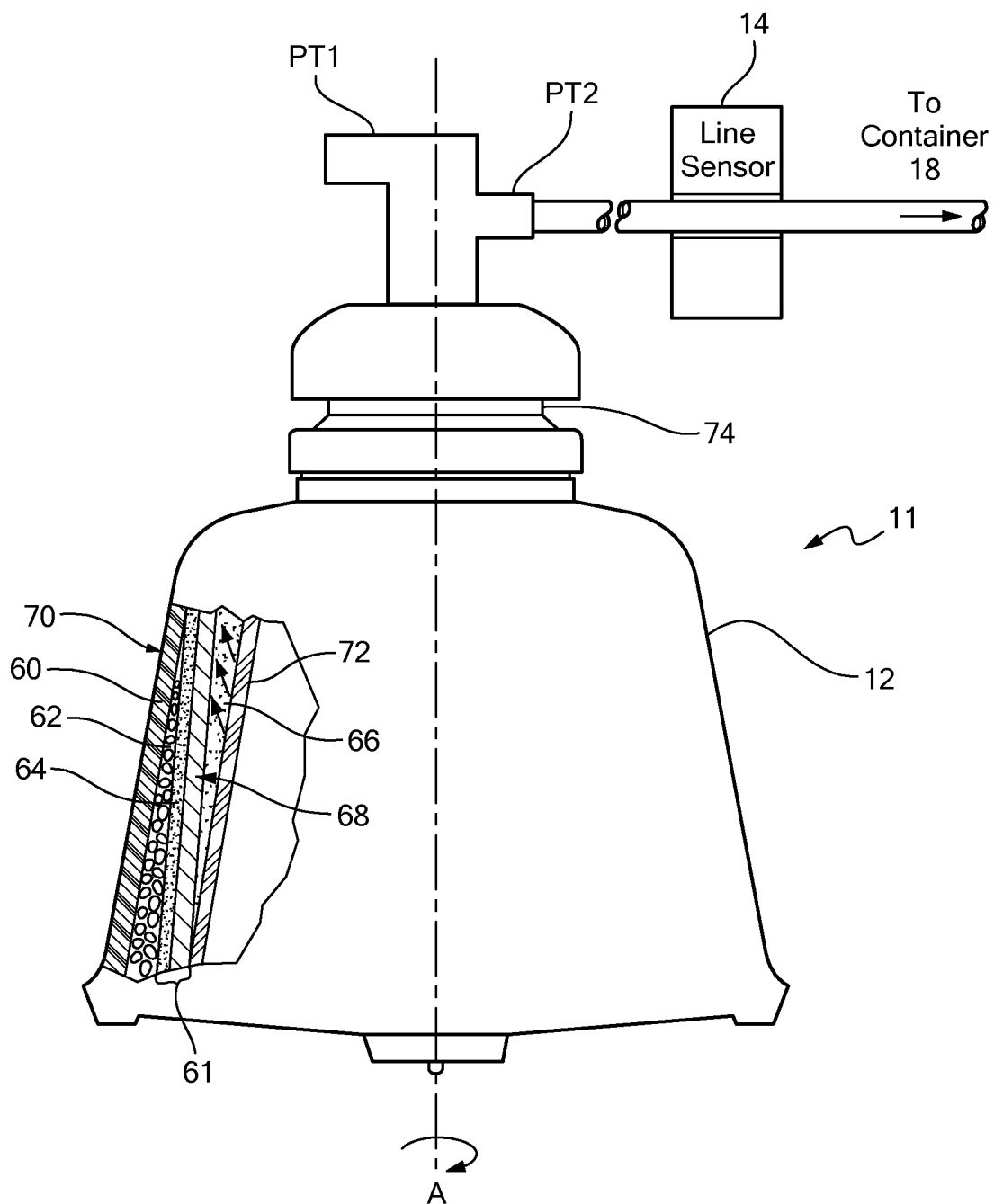
FIG. 2 is a side view of a centrifuge bowl for use with the machine of FIG. 1, in accordance with one embodiment of the invention.

Referring to FIG. 1, an apheresis apparatus 10 uses a blood component separation device, such as a standard Latham type centrifuge 11 for separating anticoagulated whole blood into its constituent components, as described in U.S. Pat. No. 3,145,713, which is hereby incorporated by reference. Other types of separation chambers and devices may be used, such as, without limitation, an integral blow-molded centrifuge bowl, as described in U.S. Pat. Nos. 4,983,156 and 4,943,273, which are also hereby incorporated by reference. The centrifuge 11 includes a rotating bowl 12 and stationary input and output ports PT1 and PT2 that are typically closely coupled to the bowl interior by a rotary seal 74 (see FIG. 2). The input port PT1 of the centrifuge 11 is in fluid communication with a venous access devices 24 (e.g., a phlebotomy needle) via, among other things, a blood filter F1, a tube 28 and a Y-connector 30, when a valve V1 is open. The venous access device 24 may be replaced with a whole blood bag (not shown) in case the whole blood is to be first pooled and then supplied. The tube 28 has compatibility with blood, as is all the tubing in the apparatus 10. The outlet port PT2 of the centrifuge 11 is selectively coupled to a number of collection containers. For example, the centrifuge 11 may be selectively coupled to a platelet rich plasma bag 18 by a tube 36, a valve V2 and a tube 37. The outlet port PT2 may also be selectively coupled to a platelet container 20 via the tube 36, a valve V3 and a tube 39. Additionally, a plasma container 22 may also be selectively coupled to the outlet port PT2 via the tube 36, a valve V4 and a tube 35. It is important to note that any of the above mentioned containers (e.g., the platelet container 20, the plasma container 22, and the PRP container 18) may be suspended by weight scales in order to help determine the amount of fluid within each of the containers.

A bag or container for storing an anticoagulant (not shown) may be in fluid communication with the venous access device/phlebotomy needle 24 via a bacteria filter F2, a tube 32 and the Y-connector 30. The bacteria filter F2 prevents any bacteria in the anticoagulant (ACD) container from entering the system. Containers 18, 20, 22, and 23 are preferably plastic bags made of a blood compatible material. Peristaltic pumps P1, P2 and P3, together with the valves V1, V2, V3, V4, V5, V6, V7, V8, and V9 control the direction and duration of flow through the apparatus 10 in response to signals generated by a line sensor 14, a donor pressure monitor (DPM) M1, a system pressure monitor (SPM) M2 and air detectors D1, D2 and D3, which detect the absence or presence of fluid. The pressure monitors M1 and M2 monitor pressure levels within the apparatus 10. The line sensor 14 is an optical sensor and detects the presence of blood components passing through the line sensor 14 from the output port PT2.

As described in greater detail below and with reference to FIGS. 4 and 5, in initial operation, the pumps P1 and P3 are energized to prime the tube 28 of the apparatus 10 with the anticoagulant. The anticoagulant passes through the filter F2 before reaching the air detector D1. The air detector D1 senses the presence of the anticoagulant at D1 and may terminate, advance, or alter the anticoagulant priming operation. After priming, the venous access device 24 may be inserted into the donor and the draw step is ready to be commenced.

Figure 3:
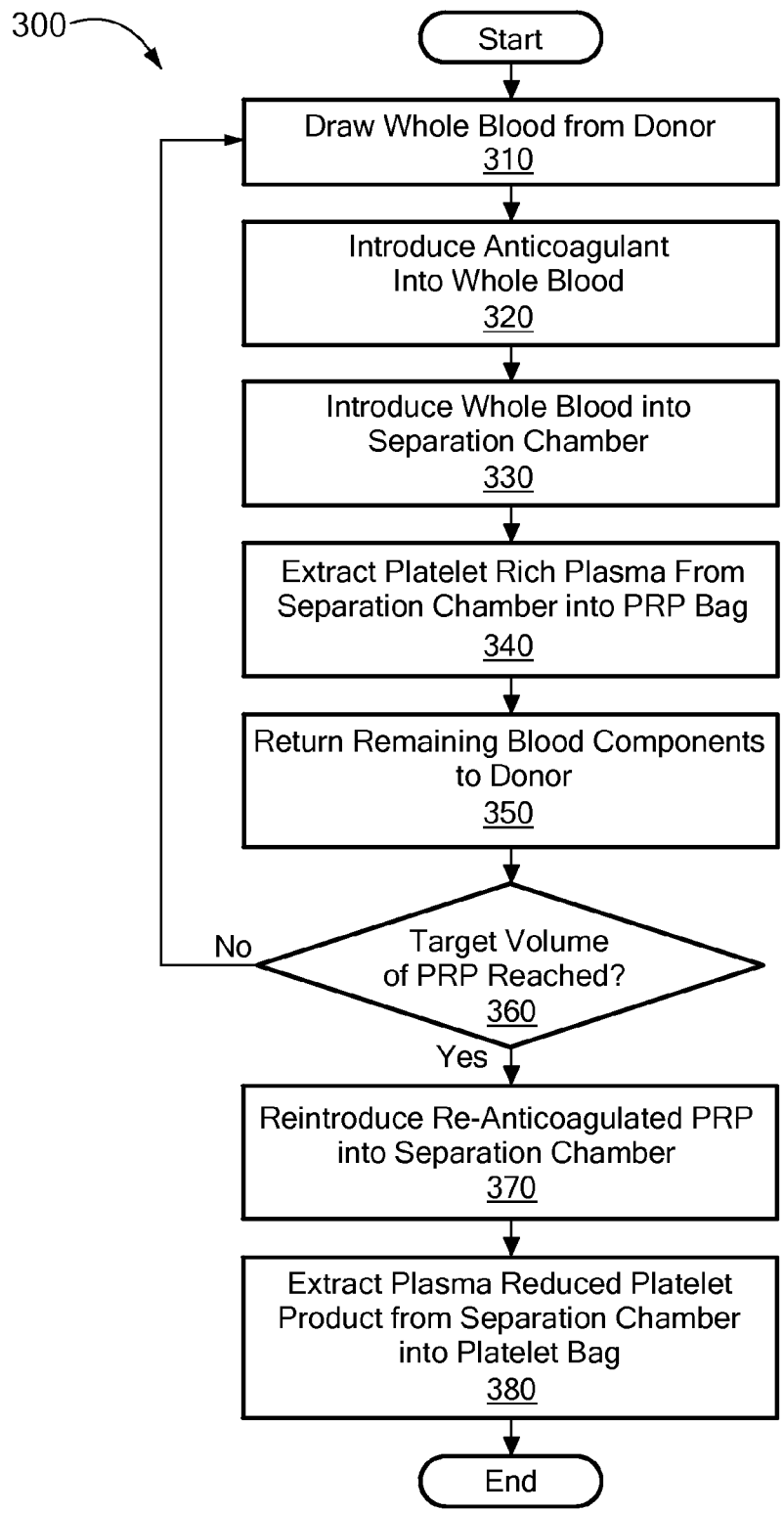
FIG. 3 is a flow chart depicting a method for collecting platelet rich plasma and plasma reduced platelet product, in accordance with one embodiment of the invention.

FIG. 3 is a flowchart depicting a method for collecting blood components (e.g., platelets) from a subject, in accordance with one embodiment of the invention. During draw step 310, whole blood is drawn from the subject, typically at a rate of about 80 ml/min. and mixed with the anticoagulant using the pumps P1 and P3 (referring back to FIG. 1) (Step 320). The pump P3 introduces and mixes the anticoagulant with the whole blood drawn from the subject (or from a bag in which it is pooled). During this time, the valve V1 is open, allowing the anticoagulated whole blood to pass through the tube 28 and blood filter F1 before being pumped into the separation device 12 through the inlet port PT1.

The anticoagulated whole blood is introduced into the bottom of the separation device 12 through a feed tube (not shown), step 330 of FIG. 3. The ratio of the anticoagulant to whole blood is typically about 1:10. However, as described in greater detail below, this ratio can be adjusted based upon the priming procedure used. The operation of each of the pumps and valves in the apheresis apparatus 10 can be performed in accordance with desired protocols under the control of a controller (not shown), which may be, for example, a microprocessor.

As mentioned above and as shown in FIG. 2, the centrifuge 11 has a fixed inlet port PT1 and a fixed outlet port PT2. The rotary seal 74 fluidly couples the stationary inlet port PT1 to the lower interior portion of the bowl 12, and the outlet port PT2 to an upper portion of the bowl interior for collecting separated fractions. A core 72 occupies a volume coaxial with the interior of bowl 12 and provides a separation region between the wall of the core 72 and the outer bowl wall 70.

As the bowl 12 is rotated, centrifugal forces separate the anticoagulated whole blood introduced into the bottom of the bowl into red blood cells (RBC), white blood cells (WBC), platelets (e.g., platelet rich plasma or "PRP") and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets/PRP 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

Returning to FIG. 1, the displaced plasma passes through the line sensor 14, the tube 36, and a 4-way connector 26, and the valve V4 (in the open position) and enters the plasma container 22. The plasma entering the plasma container 22 is drawn from the container 22 by the pump P2 via tube 42, valve V5 (in the open position), connector 92 and tube 40 from the lower port PT4 of the plasma container 22 and is recirculated into the bowl 12 through the inlet port PT1 via connector 91 and line 41. The recirculated plasma dilutes the anticoagulated whole blood entering the bowl 12 and allows the blood components to separate more readily. An optical sensor 21 is applied to a shoulder portion of the bowl 12 for monitoring each layer of the blood components as they gradually and coaxially advance toward the core 72 from the outer wall 70 of the bowl 12. The optical sensor 21 may be mounted in a position at which it can detect the buffy coat reaching a particular radius, and the steps of drawing the whole blood from the donor (Step 310) and introducing the whole blood into the bowl (Step 330) may be terminated in response to the detection.

The amount of whole blood processed by the bowl 12 may be varied in response to at least one characteristic associated with the whole blood, such as the hematocrit value, the number of platelets, the total amount of blood or the like of the whole blood, as described in U.S. Pat. No. 6,743,192 issued Jun. 1, 2004 to Sakota et al. and entitled Apheresis Apparatus and Method for Producing Blood Products, which is hereby incorporated by reference. This variable control can be implemented under the control of a microcomputer, as aforementioned. Alternatively, each of them can be implemented manually.

The platelets (e.g., platelet rich plasma or "PRP") are extracted from the bowl 12 into a PRP container 18, step 340 of FIG. 3. In extracting the platelet rich plasma ("PRP") from the bowl, various methodologies may be employed, including, without limitation, dwell, surge, and/or push methodologies. For illustrative purposes, PRP extraction based on a dwell and surge technique will now be described in detail.

After the anticoagulated whole blood has been introduced into the centrifuge 11, step 330 of FIG. 3, the valve V1 is closed and the pump P1 is stopped so that blood is no longer drawn from the donor, and dwell is commenced. During the dwell, the pump P2 recirculates plasma 66 through the bowl 12 at a moderate rate (for example, about 100 ml/min. in FIG. 4) for about 20 to 30 seconds. At this flow rate, the buffy coat 61 is diluted by the plasma and widens but the platelets/PRP do not leave the bowl 12. The dilution of the buffy coat allows the heavier white blood cells to sediment to the outer side of the buffy coat, resulting in a better separation between the lighter platelet/PRP layer 64 and the heavier white blood cells layer 62. As a result, the transitional layer 68 is reduced. The dwell period also allows the flow patterns in the bowl 12 to stabilize and allows more time for microbubbles to leave the bowl 12 and be purged.

After dwell, the surge step is commenced. In the surge, the speed of the pump P2 is increased in 5-10 ml/min. increments to recirculate plasma until reaching a platelet/PRP surge velocity of about 200-250 ml/min. The platelet/PRP surge velocity is the velocity at which platelets/PRP can leave the bowl 12 but not red blood cells or white blood cells. The plasma exiting the bowl 12 becomes cloudy with platelets/PRP and the line sensor 14 detects this cloudiness. The line sensor 14 consists of an LED which emits light through the blood components leaving the bowl 12 and a photo detector which receives the light after it passes through the components. The amount of light received by the photo detector is correlated to the density of the fluid passing through the line.

When platelets/PRP first start leaving the bowl 12, the line sensor output starts to decrease. The valve V2 is opened and the valve V4 is closed and the platelets/PRP are collected in container 18. Once the majority of the platelets/PRP are removed from the bowl 12, the fluid exiting the bowl becomes less cloudy. The line sensor 14 detects this lessening of cloudiness, whereupon valve V2 is closed.

After the platelets/PRP have been collected, return step 350 (see FIG. 3) is initiated. During return step 350, the rotation of the bowl 12 is stopped and the remaining blood components in the bowl 12 are returned to the donor by reversal of rotation of the pump P1 via the venous access device 24 with the valve V1 open. The valve V4 is also opened to allow air to enter the centrifuge bowl during the return. The plasma from the container 22 dilutes the remaining blood components in the bowl 12. In other words, the pump P2 mixes the plasma with the returning components in the bowl 12 with the valve V4 open, thereby diluting the returning red blood cells component with plasma and speeding up the return time. When the remaining blood components in the bowl have been returned to the donor, the return step 350 is terminated.

The steps of drawing whole blood from the donor, step 310, introducing anticoagulant into the whole blood, step 320, introducing the whole blood into a separation chamber, step 330, extracting platelets/PRP from the separation chamber into a container, step 340, and returning the remaining components back to the donor, step 350, are repeated until a target volume of platelets/PRP is sequestered in the container 18, step 360. Typically, steps 310-350 are repeated two to four times, with about 450-500 ml of whole blood processed per cycle. The sequestered platelet/concentration within the PRP is typically about $1.5 \times 10^6 / \mu L$.

The method 300 may then reintroduce the platelets/PRP in container 18 into the bowl 12, step 370 of FIG. 3, forming a layer of platelets/PRP that is several times larger than that obtained by processing only one cycle of whole anticoagulated blood. For example, in some embodiments, the platelet/PRP layer volume is approximately equal to the average volume of one cycle multiplied by the number of platelet/PRP sequestering cycles plus one. The platelets/PRP are drawn from port PT5 of container 18 by pump P2 via tube 43, valve V7 (in the open position), connector 93, and input into bowl 12 through the inlet port PT1 via connector 91 and line 41. To minimize contact between the platelets/PRP and bowl 12, the bowl 12 may be partly filled with anticoagulated whole blood drawn from the donor prior to re-introduction of the platelets. The whole blood forms a cell bed at the periphery of the bowl 12 that serves as a buffer between the periphery of the bowl and the platelets/PRP, reducing platelet clumping. Additionally or alternatively, whole anticoagulated blood may be added to the separation chamber during platelet/PRP reintroduction so as to bring platelet layer towards the elutriation radius, or after platelet/PRP reintroduction for perfecting platelet separation and standardizing conditions of initiating platelet extraction.

Using, for example, surge or push methodologies, a plasma reduced platelet product is extracted from the layer of platelets that now reside in bowl 12, step 380 of FIG. 3. The plasma reduced platelet product is sequestered in container 20 via line sensor 14, tube 36, connector 26, connector 50, and valve V3 (in the open position). Platelet product concentration is typically in the range of $2.6 \times 10^6 / \mu L$ to $5.2 \times 10^6 / \mu L$, which is 2-3 times that of platelets/PRP sequestered when processing only one cycle of whole anticoagulated blood.

It is important to note that during the reprocessing of the PRP collected within the PRP container 18, the platelets/PRP that are reintroduced into the separation chamber may begin to coagulate and/or clump. In order to prevent clumping and coagulation, additional anticoagulant may be added to platelets/PRP prior to reprocessing within the separation chamber 12. However, care must be taken to avoid adding too much anticoagulant because, as discussed above, if too much anticoagulant is returned to the donor, the donor may experience negative side effects. Accordingly, embodiments of the present invention utilize the initial priming step discussed above to provide the PRP with additional anticoagulant while avoiding adding additional anticoagulant to the overall system 10. FIGS. 4 and 5 show exemplary embodiments of such methods.

As shown in FIG. 4, the blood apheresis method 400 begins with priming the apheresis system, step 410. During the priming step, pumps P1 and P3 prime the anticoagulant line 32 and the donor line 28 until the anticoagulant is detected by D2. The system 10 will then continue priming the system until the donor line 28 is full of anticoagulant and a small amount of anticoagulant is transferred into the PRP container 18 via line 28, valve V1, pump P1, connector 93, line 43, and valve V7. The amount of anticoagulant transferred into the PRP container 18 may be proportional to the expected volume of PRP to be collected using the techniques described above (e.g., it may be proportional to the target volume of PRP). For example, the volume of anticoagulant within the PRP container 18 may be $1/10^{th}$ of the target PRP volume (e.g., if the target PRP volume is 300 ml, 30 ml may be transferred into the PRP container 18).

Once the system 10 is primed with anticoagulant and the desired amount of anticoagulant is within the PRP container 18, the system 10 may begin to collect the platelets/PRP (step 420), as described above with regard to FIG. 3 (e.g., the system 10 may collect the platelets/PRP using the draw, separate, and extract cycles shown in FIG. 3). As the platelets/PRP are extracted from the separation chamber 12, they will enter the PRP container 18 containing the additional anticoagulant and mix with the anticoagulant.

It should be understood that the initial concentration of anticoagulant within the PRP container 18 will be higher than the target final concentration (e.g., 1:10). However, as the system 10 collects additional platelets/PRP in each subsequent cycle, the anticoagulant concentration will decrease towards the final concentration level because, as mentioned above, the amount of anticoagulant added to the PRP container 18 may be proportional to the target volume of PRP. The process 400 may continue until the target volume of platelets/PRP is collected (step 430).

FIG. 5 shows an alternative embodiment of the priming process shown in FIG. 4. In this embodiment, the anticoagulant may be metered into the PRP container 18 as additional collection cycles are completed. In particular, once the system 10 is primed with anticoagulant and the PRP container 18 has the desired amount of anticoagulant (e.g., as discussed above) (Step 410), the system 10 may then transfer the anticoagulant in the PRP container 18 to the RBC container 23 (Step 510). The system/method 500 may transfer the anticoagulant within the PRP container 18 to the RBC container 23 using pump P1, which will transfer the anticoagulant to the RBC container 23 through valve V7 (open), line 43, connector 93, valve V9 (open), and line 49.

The system 10 may then begin to collect the platelets/PRP as described above and as shown in FIG. 3 (Step 420). If the anticoagulant prime ended with filter F1 full of anticoagulant, the system 10 may start the first draw cycle by transferring the anticoagulant within filter F1 to the RBC container 23 or back to the anticoagulant source. As discussed in greater detail below, if the anticoagulant is transferred to the RBC container, this volume should be taken into account when determining the correct amount of anticoagulant. In accordance with embodiments of the present invention, a portion of the anticoagulant within the RBC container 23 may be transferred to the PRP container 18 between the collection cycles (Step 520). For example, after the first cycle of platelets/PRP is collected, the system 10 may transfer a portion of the anticoagulant to the PRP container 18. In particular, the draw cycle will start by transferring a portion of the volume within the RBC container 23 to the PRP bag using pump P1 and pump P2 (e.g., in series). If the pump tubing segments contains blood from the prior cycle, the pump P1 will transfer the blood to the separation device 12 prior to transferring the anticoagulant to the PRP container 18.

As the system 10 approaches the end of the anticoagulant transfer (Step 520), pump P1 will start drawing the whole blood from the donor to start the next draw/collection cycle. Since the anticoagulant transfer may not yet be complete, the beginning of the next draw phase will finish the anticoagulant transfer to the PRP container 18 before the anticoagulated whole blood is directed to the bowl.

The amount of anticoagulant added to the PRP container 18 after each cycle may be proportional to the amount of platelets/PRP collected during the preceding or subsequent cycles. For example, if the total volume to be transferred into the PRP container is 30 ml (e.g., to achieve the 1:10 ratio with the target volume of collected PRP), and the platelets/PRP are collected in 5 cycles, 6 ml of anticoagulant may be added to the PRP container 18 after each cycle. This allows the system to provide sufficient anticoagulant to avoid platelet/PRP clumping/coagulation and avoid an initial high concentration of anticoagulant. The process 500 may continue until the target volume of platelets/PRP is collected (step 430). Although, the methods/system use the RBC container 23 to store the anticoagulant between cycles, once the anticoagulant is fully transferred to the PRP container 18 (e.g., after the last collection cycle), the RBC container 23 may be used for recovering pre-filter red blood cells in preservative solution.

It is important to note that, because valve V1 is closed during the transfer of anticoagulant from the PRP container 18 to the RBC container 23 (e.g., Step 510 in FIG. 5), a significant amount of anticoagulant may remain in the filter F1 (e.g., from the initial prime step). Some or all of this anticoagulant may either be transferred back to the anticoagulant source or it may be transferred to the RBC container 23. If the anticoagulant is transferred to the RBC container 23, the amount of anticoagulant should be taken into account when determining the total amount of anticoagulant within the system (e.g., to ensure that too much anticoagulant is not being return to the donor) and determining the amount of anticoagulant needed to re-anticoagulate the PRP. If the anticoagulant is returned to the anticoagulant source, it need not be taken into account.

Although the above described embodiments meter anticoagulant into the PRP container 18 in bolus transfers (e.g., either during the initial prime or between cycles of collecting the PRP), other embodiments of the present invention may continuously meter anticoagulant into the PRP and/or PRP container 18 as the system 10 collects the PRP. In other words, embodiments of the present invention may, as PRP is being extracted from the bowl 12, introduce anticoagulant into the PRP or the PRP container 18 in a manner similar to the way the system 10 introduces the anticoagulant into the whole blood as it is withdrawn from the body.

To facilitate the addition of anticoagulant directly into the PRP as it is being extracted from the bowl 12, the system 10 may have additional valving, pumps, and connectors. For example, line 36 may have an additional connector located between the line sensor 14 and the PRP container 18. This connector may be used to connect the anticoagulant source with the line 36 using an additional line. If needed, the additional line may have an additional pump to help transfer/introduce the anticoagulant into the PRP. The anticoagulant may then be introduced into the PRP as it passes through line 36.

Other embodiments, as mentioned above, may continuously meter the anticoagulant for the PRP directly into the PRP container 18. To facilitate this addition, the system 10 may have an additional connector, valve, pump, and line that connect to line 43 (e.g., in a manner similar to that described above for embodiments continuously metering anticoagulant into the PRP as it passes through line 36). This configuration allows the anticoagulant to be added to the PRP container 18 via port PT5.

It is also important to note that, because the above described re-anticoagulation methods add the additional anticoagulant directly to the platelets/PRP, embodiments of the present invention do not need to add additional anticoagulant to the overall system 10 (e.g., by adding additional anticoagulant to the whole blood as it is drawn from the donor). In order to achieve the same benefits of the embodiments of the present invention, systems adding anticoagulant to the overall system will ultimately return an additional 153 ml of anticoagulant to the donor. In other words, in order to achieve the additional 30 ml required for re-processing the platelets/PRP to obtain the plasma reduced platelet product, the ratio of anticoagulant will need to increase from 1:9 to 1:6.1, as compared to embodiments of the present invention. Accordingly, by using the above described methods, the risk of returning too much anticoagulant to the patient is greatly reduced.

It should be noted that the surge elutriation technique may use a variety of fluids other than plasma to extract either the platelets/PRP or the reduced plasma platelet product from the separation chamber (e.g., saline solution may be used).

Additionally, once the platelets and the reduced plasma platelet product are collected, a platelet additive/preservative solution may be added to help preserve and store the platelets for later use. The preservative solution can be added to the reduced plasma platelet product within the platelet container 20 after collection, or the platelet collection bag 20 and the reduced plasma platelet product bag 22 may be pre-loaded with the additive solution. To facilitate the addition of additive solution, the system 10 may include a platelet additive storage container (not shown) and a platelet additive line 45 that may be fluidly connected to platelet bag 20 via connector 46, and line 47. In a similar manner to the other lines and tubes within the system, the platelet additive line 45 may also include a valve V6 that prevents/allows flow through the platelet additive line 45. Such embodiments may also have a line 48 fluidly connecting a platelet storage bag 70 and the reduced plasma platelet product bag 20. This line may include a valve V8 and a filter F3, such as a leukoreduction filter. Once the additive solution is added, the system 10 may transfer the plasma reduced platelet product to the platelet storage container 70 for storage.

If additional reduced plasma platelet product is required, each of the steps described above (e.g., 310-380 and 410-430) may be repeated until a desired quantity of plasma reduced platelet product is collected. In various embodiments, plasma may be added to the plasma reduced platelet product so as to adjust the plasma reduced product to a predetermined volume or concentration.

It is important to note that some embodiments of the apheresis apparatus can be three-line systems having, in addition to some or all of the components discussed above, a dedicated return line, and a dedicated draw line. In such embodiments, both the return line and the draw line may have a dedicated pump that controls the flow and pressure within the lines. For example, the return line may have a dedicated return pump and the draw line may have a dedicated draw pump. In addition to the dedicated pumps, each line may also include a pressure sensor that allows the system to monitor the pressure within the lines and adjust the flow rate based on the pressure measurements.

The described embodiments of the invention are intended to be merely exemplary and numerous variations and modifications will be apparent to those skilled in the art. All such variations and modifications are intended to be within the scope of the present invention.

We claim:

1. A method for the re-anticoagulation of platelet rich plasma in a blood apheresis system, the method comprising:
   priming the blood apheresis system with anticoagulant such that a volume of anticoagulant is transferred to a PRP container, the volume of anticoagulant being proportional to a target volume of platelet rich plasma, wherein priming includes drawing anticoagulant from an anticoagulant source and through a line fluidly connecting the anticoagulant source and the PRP container; and
   collecting the target volume of platelet rich plasma within the PRP container.

2. A method according to claim 1, wherein priming the blood apheresis system with anticoagulant further includes priming an anticoagulant line and a donor line filter with anticoagulant.

3. A method according to claim 2, wherein priming the blood apheresis system further includes transferring the anticoagulant within the donor line filter to a red blood cell container.

4. A method according to claim 3, wherein the target volume of platelet rich plasma is collected in a plurality of cycles, the anticoagulant within the donor line filter transferred to the red blood cell container at the start of a first of the plurality of cycles.

5. A method according to claim 3, wherein the anticoagulant within the donor line filter is returned to an anticoagulant source.

6. A method according to claim 1, wherein the target volume of platelet rich plasma is collected in a plurality of cycles.

7. A method according to claim 6, wherein the target volume is the sum of the volumes collected in each of the plurality of cycles.

8. A method according to claim 6, wherein each of the plurality of cycles includes:
   drawing whole blood from a donor;
   introducing anticoagulant into the whole blood drawn from the donor;
   introducing the anticoagulated whole blood into a separation chamber, wherein the separation chamber separates the anticoagulated whole blood into a number of blood components including platelet rich plasma; and
   extracting the platelet rich plasma from the separation chamber into the PRP container.

9. A method according to claim 1, further comprising:
   reintroducing the platelet rich plasma from the PRP container into the separation chamber, the separation chamber separating the reintroduced platelet rich plasma into plasma and plasma reduced platelet product; and
   extracting the plasma reduced platelet product from the separation chamber into a platelet container.

10. A method according to claim 1, wherein an amount of anticoagulant introduced into the whole blood is proportionately reduced by the volume of anticoagulant within the PRP container.

* * * * *